United States Patent [19]

Fried

[11] Patent Number: 4,638,093
[45] Date of Patent: Jan. 20, 1987

[54] PREPARATION OF SECONDARY THIOLS

[75] Inventor: Herbert E. Fried, Houston, Tex.

[73] Assignee: Shell Oil Company, Houston, Tex.

[21] Appl. No.: 718,912

[22] Filed: Apr. 2, 1985

Related U.S. Application Data

[63] Continuation of Ser. No. 484,051, Apr. 11, 1983, abandoned.

[51] Int. Cl.$^4$ .......................................... C07C 149/06
[52] U.S. Cl. ..................................................... 568/73
[58] Field of Search ........................................... 568/73

[56] References Cited

U.S. PATENT DOCUMENTS

| | | | |
|---|---|---|---|
| 2,386,769 | 10/1945 | Badertscher et al. | 568/73 |
| 2,386,773 | 10/1945 | Badertscher et al. | 568/60 |
| 2,434,510 | 1/1948 | Olin et al. | 260/609 |
| 2,435,545 | 3/1948 | Lyon | 568/73 |
| 2,464,049 | 3/1949 | Mikeska | 260/609 |
| 2,502,596 | 4/1950 | Schulze | 260/609 |
| 2,610,981 | 9/1952 | Short | 568/73 |
| 2,950,324 | 8/1960 | Loev et al. | 260/609 |
| 2,951,875 | 9/1960 | Loev et al. | 260/609 |
| 3,140,322 | 7/1964 | Frilette et al. | 568/72 |
| 3,312,751 | 4/1967 | Kerr et al. | 585/638 |
| 3,534,106 | 10/1970 | Warner | 568/73 |
| 3,676,523 | 7/1972 | Mason | 260/683.15 |
| 3,686,351 | 8/1972 | Mason | 260/683.15 |
| 3,702,886 | 11/1972 | Argauer | 423/328 |
| 3,737,475 | 6/1953 | Mason | 260/683.15 |
| 3,825,615 | 7/1974 | Lutz | 260/683.15 |
| 3,963,785 | 6/1976 | Kubicek | 568/73 |
| 4,020,121 | 4/1977 | Kister | 260/683.15 |
| 4,046,859 | 9/1977 | Plank et al. | 423/328 |
| 4,102,931 | 7/1978 | Buchholz | 568/73 |
| 4,313,006 | 1/1982 | Hager | 568/70 |

FOREIGN PATENT DOCUMENTS 1188036 4/1970 United Kingdom .

Primary Examiner—Donald G. Daus
Assistant Examiner—Mary E. Ceperley
Attorney, Agent, or Firm—Richard F. Lemuth

[57] ABSTRACT

A process is disclosed for the preparation of secondary thiols by the addition of $H_2S$ to $C_{10}$ to $C_{30}$ linear olefins in the presence of certain zeolite catalysts. The process achieves high selectivity to the secondary thiol and minimizes formation of dialkyl sulfide by-products. The secondary thiol products are of particular advantage for use as intermediates in the preparation of surfactant chemicals.

10 Claims, No Drawings

PREPARATION OF SECONDARY THIOLS

This is a continuation of application Ser. No. 484,051 filed Apr. 11, 1983, now abandoned.

BACKGROUND OF THE INVENTION

The present invention relates to the preparation of secondary thiols by reaction of hydrogen sulfide with olefins having carbon numbers in the range from 10 to 30. More particularly, the invention relates to a process in which linear mono-olefins are contacted with $H_2S$ in the presence of a zeolite catalyst to form a secondary thiol product particularly suitable for use as a precursor in the manufacture of surface active detergent components.

Thiols in the $C_{10}$ to $C_{30}$ range are known compounds. Secondary thiols prepared by the process of this invention generally have utility in applications for which thiols are recognized in the art (e.g., as odorants, components of lubricant formulations, and curing agents for epoxy resins) but are further of particular advantage when used as intermediates in the synthesis of surfactant chemicals.

It is known in the prior art relevant to this invention that thiols (mercaptans) can be prepared in a process which comprises the addition of hydrogen sulfide to olefins, particularly in the presence of a catalyst, most particularly an acid catalyst. It is further recognized that this process has been applied almost exclusively to the production of tertiary thiols. Markovnikov addition of $H_2S$ to a "tertiary" olefin, usually an olefin polymer such as a propylene or butylene trimer or tetramer, results in near quantitative selectivity to the tertiary thiol. Exemplification of tertiary thiol preparation from $H_2S$ and tertiary olefin in the presence of an acidic catalyst is provided by U.S. Pat. Nos. 2,386,769, 2,434,510, 2,464,049, 2,502,596, 2,610,981, 2,950,324, 2,951,875 and 4,102,931.

The preparation of secondary thiols from higher olefins in a similar manner has not been a practical success. In one regard, the preparation of secondary thiols from linear olefins by conventional methods for $H_2S$ addition has been accompanied by the formation of substantial quantities of dialkyl sulfide by-product. The thiol is the addition product of one $H_2S$ molecule and one olefin molecule. Dialkyl sulfide is formed when the thiol, once produced, reacts with an additional molecule of the olefin. In known processes for preparing secondary thiols from $H_2S$ and higher olefins, dialkyl sulfide is formed in a quantity between about 50 and 100 percent by weight, calculated on secondary thiol. (For primarily steric reasons, dialkyl sulfide production is not a significant problem in the preparation of tertiary thiols from branched olefins.) In another regard, the catalysts and reaction conditions which are applied to promote the addition of $H_2S$ to olefins also promote double bond isomerization and/or rearrangement of the molecular structure of the olefin. As a result, olefins which might be expected to be converted to secondary thiols upon $H_2S$ addition are instead converted to tertiary thiols.

The recognition in the art of fundamental distinctions in the preparation of secondary thiols on the one hand and tertiary thiols on the other by olefin hydrosulfurization has led to processes in which an $H_2S$ addition reaction is utilized to separate tertiary olefins, which readily form thiols by addition of $H_2S$, from mixtures with other olefins which are significantly less reactive (U.S. Pat. Nos. 2,386,773 and 2,386,769).

The preparation of secondary thiols, particularly secondary thiols of linear carbon chain structure, is most important, if the thiols are to be suitable for use as intermediates in the synthesis of surface active agents. Among the surfactants which can be derived from thiols in the $C_{10}$ to $C_{30}$ range are the anionic paraffin sulfonates (molecules of the general formula $R$—$SO_3^-M^+$, where R is $C_{10}$ to $C_{30}$ alkyl and M is a cation such as sodium) which are prepared, for example, by oxidizing the thiol. Secondary thiols are particularly useful in the preparation of nonionic thiol alkoxylates (of the general formula $R$—$S(R'$—$O)_xH$, where R is again $C_{10}$ to $C_{30}$ alkyl, R' is $C_2$, $C_3$, or $C_4$ alkyl, and x is an integer between about 1 and 30), which may be prepared by the contact of the thiol with a $C_2$ to $C_4$ alkylene oxide at elevated temperature (e.g., 140° C.) and pressure (e.g., 100 psig) in the presence of an acidic (Lewis acid) or a basic (alkaline or alkaline earth metal) catalyst.

One factor of obvious importance to the use of surfactants in detergent service is their capabilities for soil removal. Surfactants produced from secondary thiols have been found to have excellent cleaning properties in a wide variety of detergent applications. Another important factor in surfactant utilization has to do with environmental considerations. In many of their common applications in both industry and the home, surfactants find their way into waste water streams. Biodegradation of the surfactant molecule then becomes of critical concern. Branched carbon chain surfactants derived from tertiary thiols are significantly less biodegradable than those surfactant molecules of linear carbon chain that are derived from secondary thiols, and, accordingly, are much less acceptable for widespread use in detergent and other common surfactant services. For this reason, an improved process for the selective preparation of secondary thiols would be particularly desirable.

With specific regard to catalysts utilized in the process of the present invention, the aforementioned U.S. Pat. No. 4,102,931 describes the use of zeolites to catalyze the addition of $H_2S$ to branched unsymmetrical olefins for preparation of tertiary thiols. Linear olefins are excluded from the starting material disclosed as useful in this prior art process, and the patent does not attribute to the zeolites any beneficial influence upon any aspect of process selectivity.

Zeolites have also been proposed (U.S. Pat. No. 4,313,006) as catalysts for the conversion of dialkyl sulfide to alkyl mercaptans by reaction with $H_2S$ at high temperature, e.g., 250°–400° C., preferably 320°–390° C.

SUMMARY OF THE INVENTION

It has now been found that secondary thiols are prepared in high selectivity by the addition of $H_2S$ to $C_{10}$ to $C_{30}$ linear olefins in the presence of certain zeolite catalysts.

Accordingly, the present invention is a process for the preparation of secondary thiols which comprises reacting a linear olefin having a carbon number in the range from about 10 to 30 with hydrogen sulfide in the presence of a catalytically effective amount of a zeolite catalyst. Process performance is further critically dependent upon the process temperature and upon the relative proportions of olefin, $H_2S$, and catalyst.

Of particular importance, this process results in production of secondary thiols in high selectivity. Problems of undesirable conversion of the olefin starting material to dialkyl sulfide and/or tertiary thiol byproducts, characteristic of all prior art processes for preparation of secondary thiols in the higher carbon number range, have been essentially eliminated.

DESCRIPTION OF THE PREFERRED EMBODIMENTS

The process of the invention is intended for limited application to the preparation of secondary thiols in the carbon number range from about 10 to 30 from corresponding $C_{10}$ to $C_{30}$ mono-olefins. Preference in this regard may be expressed for application of the invention to the conversion of olefins in the carbon number range from about 10 to 22, while an olefin reactant in the carbon number range from about 10 to 16 is more preferred, and an olefin in the carbon number range from about 10 to 14 is considered most preferred. The invention is further intended for the preparation of secondary thiols from olefins of linear (straight chain) structure. Similar processing of branched or cyclic olefins leads to the formation of significant quantities of materials other than the secondary thiols.

The process limitation concerning olefin reactants having a carbon number up to about 30 is intended to correspond to the requirement for a liquid phase reaction mixture at acceptable process temperatures. Reactants of somewhat higher carbon number may be utilized, particularly if applied in mixture with olefins of lower carbon number or if other provision is made to maintain a liquid reaction mixture.

Preferred for use as olefin reactant for the practical reason of availability are the commercial olefin products in the $C_{10}$ to $C_{30}$ range. One example of such olefins is the Chevron Alpha Olefin product series (trademark of and sold by Chevron Chemical Co.), manufactured by the cracking of paraffin wax. Commercial production is more commonly accomplished by the oligomerization of ethylene using procedures well known to the art. The resulting oligomerization products are substantially of linear structure and thus products are substantially of linear structure and thus readily distinguishable from the highly branched propylene and butylene oligomers (or polymers) conventionally used to prepare tertiary thiols. Commercial olefin products manufactured by ethylene oligomerization are marketed in the United States by Gulf Oil Chemicals Company under the trademark Gulfene, by Shell Chemical Company under the trademark Neodene and by Ethyl Corporation as Ethyl Alpha-Olefins. Specific procedures for preparing suitable linear olefins from ethylene are described in U.S. Pat. Nos. 3,676,523, 3,686,351, 3,737,475, 3,825,615 and 4,020,121. While most of such olefin products are comprised largely of alpha-olefins, higher linear internal olefins are also commercially produced, for example, by the chlorination-dehydrochlorination of paraffins, by paraffin dehydrogenation, and by isomerization of alpha-olefins. An olefin starting material containing a major proportion of internal olefins is particularly preferred as starting material in the process of the invention, from the standpoint of selectivity to secondary thiol. Linear internal olefin products in the $C_{10}$ to $C_{30}$ range are marketed by Shell Chemical Company and by Liquichemica Company. These commercial products, whether predominantly internal or alpha-olefins typically contain about 70 percent by weight (% w) or more, most often about 80% w or more, linear mono-olefins in a specified carbon number range (e.g., $C_{10}$ to $C_{12}$, $C_{11}$ to $C_{15}$, $C_{12}$ to $C_{13}$, $C_{15}$ to $C_{18}$, etc.), the remainder of the product being olefin of other carbon number or carbon structure, diolefins, paraffins, aromatics, and other impurities resulting from the synthesis process. Commercial olefins consisting essentially of (i.e., containing at least about 90% w) linear mono-olefins in the specified carbon number range are considered most preferred for use as reactant in the process of the invention.

The $H_2S$ reactant is suitable obtained from any convenient source, although it is preferably in a relatively pure form. It is particularly important that the $H_2S$ reactant and the reaction system as a whole be essentially free of water, the presence of which is found to result in loss of catalyst activity. Lewis bases and organic peroxides should also be eliminated from the reaction system.

For purposes of this invention, the olefin and $H_2S$ reactants are contacted in the presence of a catalytically effective amount of one or more of certain zeolites. As the terminology is understood in the art and as it is used herein, the zeolites are a family of crystalline aluminosilicates well defined both as to chemical composition and physical structure. Chemically, the zeolites may be represented by the formula

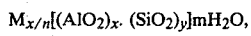

$$M_{x/n}[(AlO_2)_x \cdot (SiO_2)_y]mH_2O,$$

wherein M is a cation of valence n. Structurally, $AlO_4$ and $SiO_4$ groups are linked by shared oxygen atoms in a three dimensional network forming intracrystal cavities interconnected by smaller channels, or pores. Cations and water molecules are bound to the aluminosilicate framework within the cavities. The various zeolites differ one from the other principally in terms of the proportion of Al to Si, the identity of the cation, the configuration of the three dimensional alumina and silica network, and the particular size and shape of the crystal pores and cavities.

Two aspects of the zeolites, one relating to structure and the other to composition, have been found to be critical to their successful application as the catalyst in the process of the invention. In terms of structure, the pore openings of a suitable zeolite necessarily have a diameter of at least about 4 Å, and are preferably of a diameter no greater than about 9 Å. Particularly preferred is a zeolite having pore openings between about 5 and 9 Å, while a zeolite with a pore diameter in the range from about 5 to 8.5 Å is considered to be optimal. Type X and Type Y zeolites, and zeolites of the ZSM series are specific examples of synthetic zeolites having pore openings in this most preferred range. Also suitable for use in the invention are natural (or mineral) zeolites having the specified pore opening, such as mordenite, for example. In terms of composition, the zeolite is necessarily of relatively high acidity, a requirement which relates to the nature of the cation present in the alumina and silica network. The monovalent alkali metal cation (e.g. $Na^+$ or $K^+$) form in which the synthetic zeolites are commonly found or produced does not possess the necessary acidity. However, exchange can be carried out, under procedures well known in the art, to replace the alkali metals with certain other cations and to thereby impart to the zeolite activity and the desired high selectivity for thiol preparation when applied according to the invention. Particularly suitable for purposes of the invention are decationized, or protonated, zeolites and zeolites having one or more cations selected from the group consisting of magnesium and the rare earth metals (elements of atomic numbers 21, 39 and 57 to 71, inclusive). Cation exchange can be accomplished simply by contacting the zeolite at elevated temperature (e.g., 100° C.) with a series of aqueous solutions containing the desired replacement cation. Decationized zeolites may be prepared by an exchange with an ammonium ion, followed by heating to a temperature of about 550° C. Cation exchange procedures typically result in replacement of between about 70 and 95% of the zeolite cations.

As examples of specific synthetic zeolites preferred for use in this invention mention may be made of commercial products marketed by Union Carbide Corporation, particularly the decationized Y zeolites known as Linde LZ-Y62, LZ-Y72, and LZ-Y82, and the rare earth impregnated Y zeolite Linde SK-500. Other examples are the ZSM zeolites produced by Mobil Corporation (e.g., ZSM-4, ZSM-5, ZSM-11, ZSM-12, and ZSM-38) the preparation and properties of which are illustrated, for instance, by U.S. Pat. Nos. 3,702,886 and 4,046,859. Examples of preferred natural or mineral zeolites include cation-exchanged or decationized mordenite, ferrierite, gmelinite, cancrinite, heulandite, and dachiardite. Mordenite is particularly preferred.

Prior to use, the catalyst is preferably calcined, for instance, by heating to a temperature between about 250° and 750° C. for several hours to remove adsorbed water. A temperature of about 500° C. has been found to be particularly useful. Calcination may not be necessary for a freshly obtained zeolite, but should be carried out if the catalyst has been exposed to air or water.

For practice in accordance with the invention, $H_2S$ and olefin are contacted in the liquid phase with the solid catalyst under necessarily restricted conditions of temperature, pressure, and relative proportions of catalyst and reactants.

Contact between the olefin and $H_2S$ takes place in the liquid phase. For purposes of achieving high selectivity to the secondary thiol, it is critical that this liquid phase contain $H_2S$ and olefin in a molar ratio of at least 1 to 1. Depending upon temperature and pressure, the reaction zone may also contain an $H_2S$-rich vapor phase, although only the $H_2S$ present in the liquid phase is included in calculating the necessary molar ratio relative to olefin. Higher selectivity to secondary thiol is generally realized with increases in the $H_2S$ to olefin molar ratio above 1 to 1. For this reason, an $H_2S$ to olefin ratio in the liquid phase of at least about 2.0 to 1 by mole is preferred, a ratio of at least about 3.0 to 1 by mole is more preferred, and a ratio of at least about 5.0 to 1 by mole, particularly at least 10.0 to 1, is considered most preferred.

The process is suitably carried out only within a limited range of temperatures. To some extent, suitable process temperature is dependent upon the particular nature of the olefin reactant. In the case of a reactant which is comprised substantially of internal olefin, a temperature in the range from about 40° to 140° C. is very suitable, and a temperature in the range from about 50° to 120° C., particularly from about 60 to 100° C., is preferred. For a reactant comprised substantially of alpha-olefin, the process can be conducted in the same 40° to 140° C. range, although desired selectivity is then realized only at somewhat higher ratios of $H_2S$ to olefin, i.e., ratios greater than about 1.5 to 1 by mole, particularly greater than about 5.0 to 1 by mole. Preference is given to the processing of alpha-olefins at a temperature from about 50° to 100° C., particularly to a temperature from about 60° to 85° C. In each case, the $H_2S$ addition reaction does not proceed at appreciable rate at temperatures below 40° C., while at temperatures above about 140° C. the process does not realize the desired high selectivity to secondary thiol at desirable process pressures.

The invention is necessarily carried out under pressure, preferably at a pressure greater than about 250 psig, although somewhat lower pressures (e.g., at least about 150 psig) may be suitable at the lower process temperatures. Attention to such limitations on process pressure is critical to the successful practice of the invention. An increase in pressure, at a given temperature, is beneficial to the selective production of the secondary thiols, since it provides opportunity for maintaining a higher $H_2S$ to olefin molar ratio in the liquid phase. Considered to be particularly preferred from the standpoint of both process selectivity and processing convenience is a pressure in the range from about 350 psig, and particularly from about 400 psig, to about 1500 psig, while a pressure in the range from about 600 psig, and particularly from about 800 psig, to about 1500 psig is still more preferred. Preferences expressed with regard to upper limits on process pressure relate to aspects of practical equipment design rather than to process performance, and significantly higher pressures can be applied if desired.

The olefin and $H_2S$ are contacted in the presence of a quantity of the catalyst which is effective for promoting the desired conversion to thiol. In quantitative terms, and using a batch process and a powered catalyst as an example, a catalytically effective amount of the zeolite is ordinarily in excess of about 3 percent by weight (% w), calculated on the weight of the olefin reactant. Larger amounts of the catalyst, e.g., greater than about 6% w are usually preferred from the standpoint of enhanced reaction rate and selectivity to secondary thiol, while still larger amounts, e.g., greater than about 10% w, particularly greater than about 20% w, are more preferred. As a general rule, larger quantities will be necessary if the catalyst is applied in pellet or extrudate, rather than powdered form.

As a specific example of procedures which can be applied in the practice of the invention, liquid $H_2S$ and liquid olefin in suitable relative proportions are continuously mixed at low temperature, heated to the desired process temperature and passed through one or more contained beds of the catalyst. The process is equally adaptable to a batch mode of operation, for instance, one in which the liquid $H_2S$ and olefin mixture is added to a reaction zone containing a suitable quantity of catalyst and maintained at the desired process temperature with agitation. Other suitable processing alternatives will be apparent to those skilled in the chemical processing arts. Under preferred conditions of temperature and pressure and relative proportions of reactants and catalyst, essentially complete conversion of olefin to thiol is typically achieved in about 2 to 15 hours, often in about 3 to 7 hours.

Thiol product is suitably recovered from the process product mixture by generally conventional methods. For example, $H_2S$ reactant is effectively flash evaporated from the liquid thiol at near atmospheric pressure and at a temperature of about 125° C. Stripping with an inert gas, such as nitrogen, promotes $H_2S$ removal. The remaining liquid may be vacuum distilled to separate thiol product from the typically higher boiling by-product compounds, particularly the dialkyl sulfides.

The product of the process of the invention is a secondary thiol of the formula

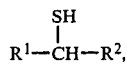
$$R^1-\underset{\underset{\displaystyle }{|}}{\overset{\overset{\displaystyle SH}{|}}{C}H}-R^2,$$

wherein $R^1$ and $R^2$ are each alkyl. $R^1$ and $R^2$, together with the carbon atom to which the SH moiety is attached, form a linear chain of between 7 and 30 carbon atoms. Position of the SH substitution along this chain is to some extent dependent upon the position of the double bond in the olefin starting material. However, it is observed that during practice of the invention isomerization of the olefin, with respect to double bond position, occurs at a rate that is roughly equivalent to the rate of $H_2S$ addition, producing a product in which the position of SH substitution is largely random. Such double bond isomerization necessitates the use of a linear olefin reactant to insure selective production of secondary rather than tertiary thiols. Moreover, the use of the linear olefin in the process of the invention is found to be sufficient to result in production of essentially only the secondary thiol. Although the starting material is subject to double bond isomerization, it is not found to undergo any significant degree of rearrangement in the carbon structure to form a tertiary olefin which would in turn yield the tertiary rather than the secondary thiol.

The invention is further illustrated by the following Examples, representing practice under certain preferred embodiments of the process of the invention.

EXAMPLES 1-12

A series of examples of the process of the invention was carried out in a batch mode. For each experiment, measured amounts of an olefin starting material and a rare earth impregnated Y-zeolite (Linde SK-500) were introduced into an autoclave reactor. Several olefin reactants, differing in carbon number and double bond position, were used. The catalyst was in the form of an extrudate, and contained 10.7% w mixed rare earth oxides. To eliminate variations in activity caused by exposure to water or air the catalyst was calcined before use (i.e., at a temperature of 500° C. for about 12 hours). Precautions were also taken in loading the olefin and catalyst to maintain the autoclave and its contents essentially oxygen and water-free. Following introduction of catalyst and olefin, the autoclave was sealed, purged with an inert gas, and then cooled to $-70°$ C. $H_2S$ reactant, in liquid form, was added at this temperature. Sufficient $H_2S$ was added to give a molar ratio of total $H_2S$ in the autoclave to total olefin in the autoclave of at least 3.3. In each case the molar ratio of $H_2S$ to olefin in the liquid phase in the autoclave was calculated to be greater than 1.0. The autoclave was then heated to the desired process temperature and autoclave pressure (maximum process pressure) was determined. (In each case, this pressure was in the range from about 350 to 800 psig.) Essentially constant temperature was maintained for a desired time by controlled cooling of the reactor. Analysis of the resulting liquid reaction mixture was conducted, after flashing or stripping off excess $H_2S$ reactant. Conversion of olefin starting material was determined by gas-liquid chromatography. Selectivity to secondary thiol was determined either by gas-liquid chromatography or by titration with silver nitrate. Dialkyl sulfide by-product was determined by HPLC analysis. Results of Examples 1-12 are presented in Table I.

TABLE I

| Example No. | $H_2S$ to olefin* molar ratio | Catalyst (weight percent on olefin) | Temp. (°C.) |
| --- | --- | --- | --- |
| 1[a] | 8.33 | 29.33 | 100 |
| 2[b] | 8.25 | 33.3 | 60 |
| 3[c] | 17.18 | 33.3 | 60 |
| 4[a] | 8.33 | 29.8 | 60 |
| 5[a] | 8.88 | 29.8 | 60 |
| 6[d] | 8.33 | 29.8 | 60 |
| 7[b] | 8.25 | 33.3 | 60 |
| 8[b] | 8.25 | 33.3 | 60 |
| 9[c] | 8.25 | 33.3 | 60 |
| 10[e] | 8.25 | 33.3 | 60 |
| 11[e] | 3.30 | 33.3 | 60 |
| 12[e] | 3.30 | 33.3 | 60 |
| 13[a] | 50 | 33.3 | 100 |

| Example No. | Reaction time (hours) | Olefin Conversion | Selectivity to thiol |
| --- | --- | --- | --- |
| 1 | 4 | 99 | 82 |
| 2 | 4 | 99 | 95 |
| 3 | 4 | 99 | 90 |
| 4 | 24 | 99 | 95 |
| 5 | 5 | 99 | 91 |
| 6 | 23 | 93 | 86 |
| 7 | 17 | 97 | 96 |
| 8 | 4 | 99.9 | 95 |
| 9 | 4 | 95 | 90 |
| 10 | 4 | 87 | 90 |
| 11 | 72 | 99 | 84 |
| 12 | 72 | 99 | 91 |
| 13 | 2.5 | 95 | 95 |

*calculated on the basis of the total weight of $H_2S$ and the total weight of olefin added to the autoclave.
[a] $C_{16}$ internal olefin reactant
[b] $C_{12}$ internal olefin reactant
[c] $C_{14}$ internal olefin reactant
[d] $C_{16}$ alpha-olefin reactant
[e] $C_{12}$ alpha-olefin reactant

EXAMPLE 14

A continuous process in accordance with the invention was carried out by passing a mixture of $C_{11}/C_{12}$ internal olefin and liquid $H_2S$, at a temperature of about 60° C. and a pressure of about 600 psig, through a contained bed of a decationized Y zeolite (Linde LZY-82). The molar ratio of $H_2S$ to olefin was about 20 to 1 in the feed (all liquid phase) entering the bed. Flowrate of reactants was controlled to give a liquid hourly space velocity of about 1.0, calculated on olefin. Under these conditions, conversion of olefin was essentially complete, with a selectivity to thiol of about 98%.

I claim as my invention:

1. A process for the preparation of $C_{10}$ to $C_{22}$ secondary thiols in enhanced selectivity which comprises contacting in a liquid phase at a temperature in the range from about 50° to 100° C. and at a pressure in the range from about 400 to about 1500 psig, one or more $C_{10}$ to $C_{22}$ linear mono-olefins with hydrogen sulfide, the molar ratio of said hydrogen sulfide to said olefins in said liquid phase being at least about 10.0 to 1, in the presence of a catalytically effective amount of a decationized or cation exchanged Type Y zeolite catalyst.

2. The process of claim 1, wherein the contact takes place in the presence of a catalytically effective amount of a decationized zeolite or a cation exchanged zeolite wherein the replacement cation is selected from the group consisting of magnesium and the rare earth metals.

3. The process of claim 2, wherein the contact takes place at a temperature from about 60° to 85° C.

4. The process of claim 2, wherein the contact takes place at a pressure in the range from about 600 psig to about 1500 psig.

5. The process of claim 4, wherein the contact takes place at a pressure in the range from about 800 psig to about 1500 psig.

6. A process for the preparation of $C_{10}$ to $C_{22}$ secondary thiols in enhanced selectivity which comprises contacting in a liquid phase at a temperature in the range from about 50° to 100° C. and at a pressure in the range from about 400 to about 1500 psig, one or more $C_{10}$ to $C_{22}$ linear internal mono-olefins with hydrogen sulfide, the molar ratio of said hydrogen sulfide to said olefins in said liquid phase being at least about 10.0 to 1, in the presence of a catalytically effective amount of a decationized or cation exhanged Type Y zeolite catalyst.

7. The process of claim 6, wherein the contact takes place in the presence of a catalytically effective amount of a decationized zeolite or a cation exchanged zeolite wherein the replacement cation is selected from the group consisting of magnesium and the rare earth metals.

8. The process of claim 7, wherein the contact takes place at a temperature from about 60° to 85° C.

9. The process of claim 7, wherein the contact takes place at a pressure in the range from about 600 psig to about 1500 psig.

10. The process of claim 9, wherein the contact takes place at a pressure in the range from about 800 psig to about 1500 psig.

* * * * *